(12) United States Patent
Taras et al.

(10) Patent No.: US 6,875,215 B2
(45) Date of Patent: Apr. 5, 2005

(54) DISTRACTION PIN FOR FRACTURE FIXATION

(75) Inventors: John Stanley Taras, 42 Landing Ct., Moorestown, NJ (US) 08057; Dennis L. Steffen, Tavernier, FL (US)

(73) Assignee: John Stanley Taras, Moorestown, NJ (US)

( * ) Notice: Subject to any disclaimer, the term of this patent is extended or adjusted under 35 U.S.C. 154(b) by 27 days.

(21) Appl. No.: 10/076,678

(22) Filed: Feb. 15, 2002

(65) Prior Publication Data

US 2003/0158556 A1 Aug. 21, 2003

(51) Int. Cl.[7] .............................................. A61B 17/56
(52) U.S. Cl. ...................................................... 606/73
(58) Field of Search ........................... 411/1–7; 606/53, 606/60, 62–68, 72, 73, 104

(56) References Cited

U.S. PATENT DOCUMENTS

| | | | | |
|---|---|---|---|---|
| 2,165,011 A | | 7/1939 | Rosenberg ..................... 85/47 |
| 2,382,019 A | | 8/1945 | Miller ........................... 85/41 |
| 3,051,169 A | * | 8/1962 | Grath ........................... 606/65 |
| 3,463,209 A | | 8/1969 | Podolsky ...................... 145/50 |
| 3,915,162 A | | 10/1975 | Miller .......................... 128/92 |
| 4,175,555 A | | 11/1979 | Herbert ........................ 128/92 |
| 4,463,753 A | | 8/1984 | Gustilo ......................... 128/92 |
| 4,564,324 A | | 1/1986 | Leibhard ....................... 411/3 |
| 4,673,323 A | | 6/1987 | Russo .......................... 411/387 |
| 4,870,957 A | * | 10/1989 | Goble et al. ................... 606/73 |
| 5,019,079 A | | 5/1991 | Ross ............................ 606/72 |
| 5,129,901 A | * | 7/1992 | Decoste ........................ 606/65 |
| 5,139,400 A | | 8/1992 | Muhling et al. ............... 606/73 |
| 5,354,299 A | | 10/1994 | Coleman ...................... 606/73 |
| 5,433,719 A | | 7/1995 | Pennig ......................... 606/73 |
| 5,499,892 A | * | 3/1996 | Reed ............................ 411/5 |
| 5,540,531 A | | 7/1996 | Choiniere .................... 411/387 |
| 5,562,671 A | * | 10/1996 | Goble et al. ................... 606/73 |
| 5,593,410 A | | 1/1997 | Vrespa ......................... 606/73 |
| 5,609,595 A | | 3/1997 | Pennig ......................... 606/73 |
| 5,645,547 A | | 7/1997 | Coleman ...................... 606/73 |
| 5,709,687 A | | 1/1998 | Pennig ......................... 606/73 |
| 5,713,705 A | * | 2/1998 | Grunbichler .................. 411/5 |

(Continued)

FOREIGN PATENT DOCUMENTS

| | | | | |
|---|---|---|---|---|
| EP | 0 276 153 A2 | * | 7/1988 | ........... A61B/17/58 |
| WO | WO 9002526 A1 | * | 3/1990 | ........... A61B/17/58 |

Primary Examiner—Anhtuan T. Nguyen
Assistant Examiner—Jessica R. Baxter
(74) Attorney, Agent, or Firm—Gordon & Jacobson, PC

(57) ABSTRACT

An internal fixation pin comprises first and second portions with threads of different diameters, but having the same pitch and thread depth. The first portion includes a self-tapping tip. No enlarged head portion is provided to the pin at the end opposite the tip. A non-threaded shaft portion is frangibly connected to the second portion and is a mechanism for rotating the pin for threaded insertion into bone. A plurality of circumferentially spaced-apart longitudinal grooves are provided on the second portion adjacent its intersection with the shaft portion. After insertion of the first and second portions across a fracture, the shaft portion is removed. The grooves permit rotation of the pin for removal should removal be necessary. A driver for pin removal is also provided, as well as a mill tool.

21 Claims, 3 Drawing Sheets

U.S. PATENT DOCUMENTS

| | | | | |
|---|---|---|---|---|
| 5,743,912 A | * | 4/1998 | Lahille et al. | 606/65 |
| 5,779,704 A | | 7/1998 | Kim | 606/64 |
| 5,868,572 A | * | 2/1999 | Lazzara et al. | 433/173 |
| 5,871,486 A | * | 2/1999 | Huebner et al. | 606/73 |
| 5,893,850 A | | 4/1999 | Cachia | 606/72 |
| 5,904,685 A | | 5/1999 | Walawalkar | 606/73 |
| 6,001,101 A | | 12/1999 | Augagneur et al. | 606/73 |
| 6,004,349 A | * | 12/1999 | Jackson | 606/61 |
| 6,019,762 A | | 2/2000 | Cole | 606/72 |
| 6,030,162 A | | 2/2000 | Huebner | 411/413 |
| 6,045,554 A | | 4/2000 | Grooms et al. | 606/73 |
| 6,074,149 A | | 6/2000 | Habermehl et al. | 411/442 |
| 6,086,303 A | | 7/2000 | Fluckiger | 411/399 |
| 6,193,719 B1 | * | 2/2001 | Gournay et al. | 606/61 |
| 6,283,973 B1 | | 9/2001 | Hubbard et al. | 606/104 |
| 6,302,888 B1 | * | 10/2001 | Mellinger et al. | 606/73 |
| 6,454,772 B1 | * | 9/2002 | Jackson | 606/73 |
| 2003/0074002 A1 | * | 4/2003 | West, Jr. | 606/73 |

* cited by examiner

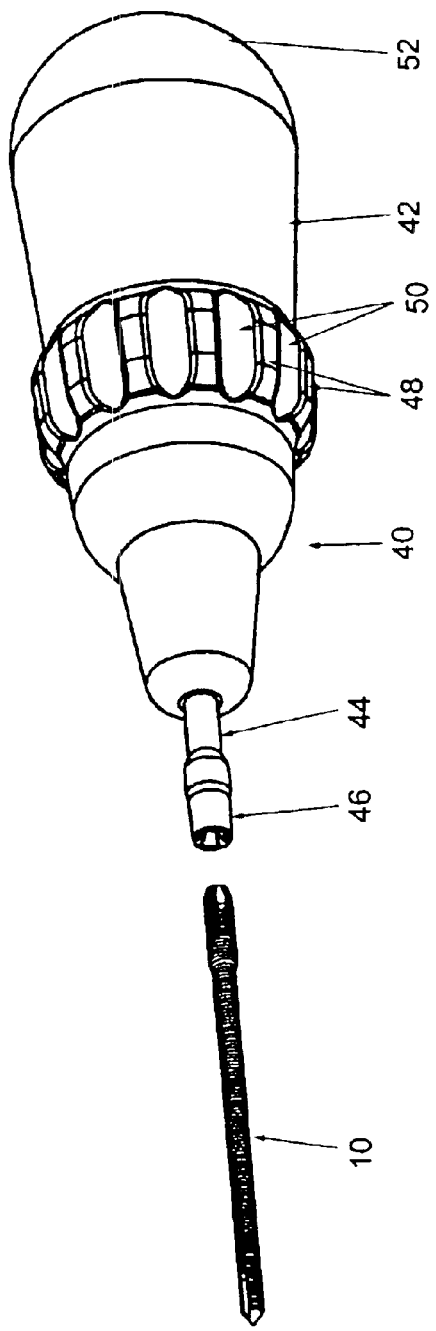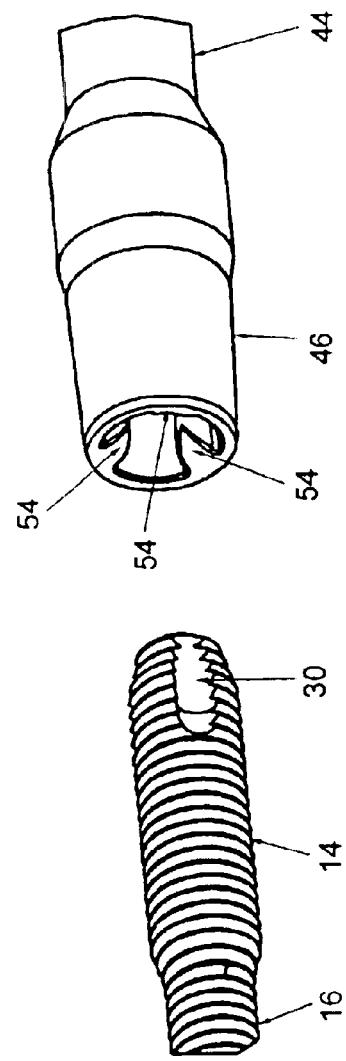
Fig. 4
Fig. 5

DISTRACTION PIN FOR FRACTURE FIXATION

BACKGROUND OF THE INVENTION

1. Field of the Invention

This invention relates broadly to orthopedic fixation devices. More particularly, this invention relates to threaded pins for treatment of fractures, particularly of the distal radius bone.

2. State of the Art

Treatment of bone fractures, and particularly distal radius fractures, depends on the type of fracture. In a distal radius, Type I fractures include an undisplaced non-articular fracture of the distal radius that defines a distal radius fragment. Type I fractures do not require reduction or are stable post-reduction. Type II fractures include a medial/lateral or volar/dorsal non-articular displaced fracture which also defines a distal radius fragment. Type II fractures are reducible closed, but remain unstable.

Type I fractures are typically treated with casting. Casting provides immobilization and the traditional immobilization period is six to eight weeks, followed by a course of physiotherapy to restore range of motion. The length of the immobilization and the resulting loss of range of motion is undesirable to many patients, including athletes, artists, musicians, and patients with an economic urgency to return to work.

Current treatment of Type II fractures includes inserting a threaded pin across the fracture. However, pin implantation is not always entirely successful. One drawback with many threaded pins in treating distal radius fractures is that their blunt tips will not always engage the radius shaft cortex and will slide into the intramedullary canal, thereby limiting the amount of proximal purchase of the pin. This is a particular concern with fractures of older osteoporotic bone. In these patients, better purchase would allow more aggressive physiotherapy. In addition, the threaded fixation pins adapted for treatment of distal radius fractures are available in a single length and thus need to be cut after insertion. The cut ends of the pins interfere with early range of motion and, to a limited extent, irritate the subcutaneous tissue and may interfere with extensor tendon function. Moreover, as the pins protrude above the bone surface, a second operation is require to remove the pins.

SUMMARY OF THE INVENTION

It is therefore an object of the invention to provide a fixation device for the treatment of Type I fractures that require early mobilization and Type II fractures that are reducible closed but unstable.

It is another object of the invention to provide a fixation device that permits immediate post-operative range of motion.

It is a further object of the invention to provide a fixation device that is adapted for increased purchase in the bone.

It is an additional object of the invention to provide a fixation device that will not irritate subcutaneous tissue or interfere with extensor tendon function.

It is also an object of the invention to provide a fixation device that does not require removal after insertion.

It is still another object of the invention to provide a fixation device that is relatively easy to insert into bone.

It is yet another object of the invention to provide a fixation device particularly adapted for treatment of distal radius fractures, and which may also be used for the treatment of other fractures, such as olecranon fractures and malleolus fractures.

In accord with these objects, which will be discussed in detail below, an internal fixation device comprises a threaded pin having first and second longitudinal portions. The first portion has a first diameter and threads of a first thread diameter, and the second portion has a relatively larger second diameter and threads of a relatively larger second thread diameter.

According to a preferred aspect of the invention, the threads on each of the first and second portions have the same pitch and thread depth. The first portion includes a self-tapping tip adapted to provide increased purchase in the radial shaft cortex. No enlarged head portion is provided to the pin at the end opposite the tip.

According to another preferred aspect of the invention, a preferably non-threaded shaft portion is frangibly connected to the second portion and is a means by which to rotate the pin for threaded insertion into bone. In particularly, the shaft portion is adapted to be received in a chuck of a drill device such that the pin may be rotated by the drill device. In order to facilitate decoupling of the shaft portion from the second portion (i.e., after pin insertion), a circumferential channel is preferably provided at the intersection of the second portion and the shaft portion.

According to yet another preferred aspect of the invention, the second portion is provided with a plurality of, and preferably three, circumferentially spaced-apart longitudinal grooves adjacent its intersection with the shaft portion.

In use, the pin is held by the shaft portion and rotatably inserted into bone across the fracture. The self-tapping tip facilitates initial insertion into the bone as well as purchase of the tip of the pin in the radial shaft cortex. The threads on the first portion provide a stable engagement with the shaft of the bone proximal of the fracture. The wider threads at the second portion provide superior purchase on the distal fragment of bone located distal of the fracture. In addition, the headless design does not cause the distal fragment to be compressed against the radial shaft from which it separated. Further, by providing the first and second portions with threads of the same pitch and thread depth, the reduction of the fracture provided by the physician is not disturbed or acted against by the screw, but rather maintained. The pin is inserted until the second portion is flush with or slightly recessed into the distal fragment. The shaft of the pin is then removed from the pin, e.g., by bending or cutting.

The plurality of grooves at the second portion provide a means for rotating the pin after the shaft is removed, as described below. Thus, should pin removal be necessary after insertion, the headless pin can be retrieved. To that end, a driver device including a handle and a shaft provided with a socket is provided. The socket is adapted to be positioned over the end of the second portion of the pin (after the shaft has been removed) and to rotationally interfere with the grooved end of the second portion of the pin. As such, rotation of the driver permits removal of the pin from bone after the pin has been threadably inserted flush with or recessed into the distal fragment bone.

The pin may be used to treat olecranon fractures, malleolus fractures, and fractures of similar bones, and provides the same above described advantages when used therefor.

Additional objects and advantages of the invention will become apparent to those skilled in the art upon reference to the detailed description taken in conjunction with the provided figures.

BRIEF DESCRIPTION OF THE DRAWINGS

FIG. 4 is an exploded perspective view of the pin, with shaft removed, and the driver device of the invention;

FIG. 5 is an enlarged broken perspective view of a second portion of the pin and a socket of the driver.

DETAILED DESCRIPTION OF THE PREFERRED EMBODIMENTS

Figure 1:
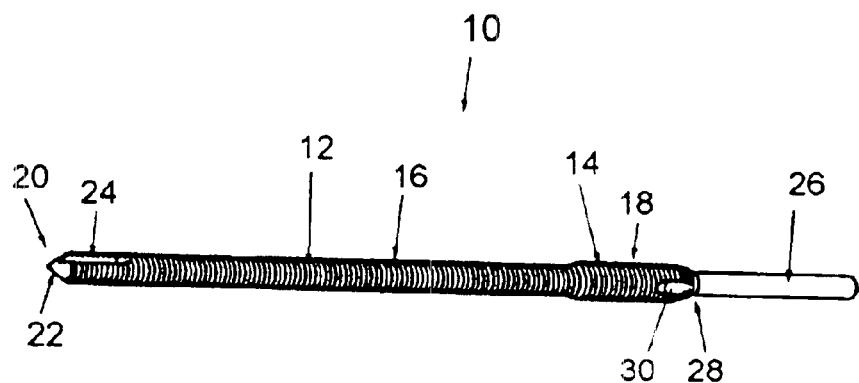
FIG. 1 is a perspective view of a distraction pin according to the invention.
Figure 2:
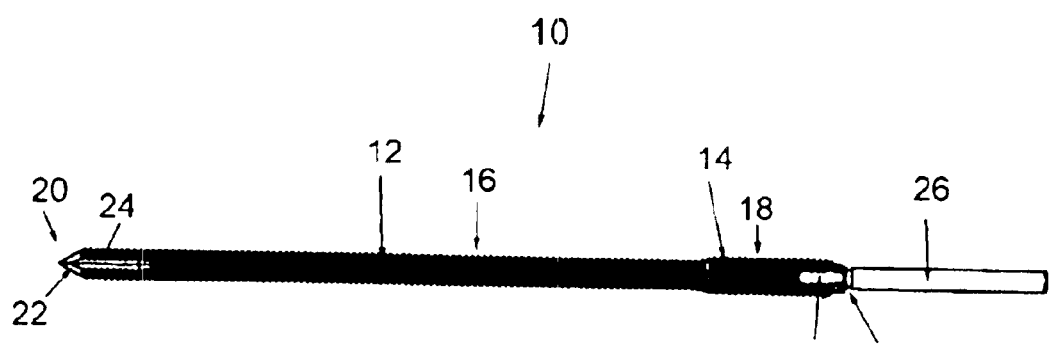
FIG. 2 is a side elevation view of the distraction pin according to the invention.
Figure 3:
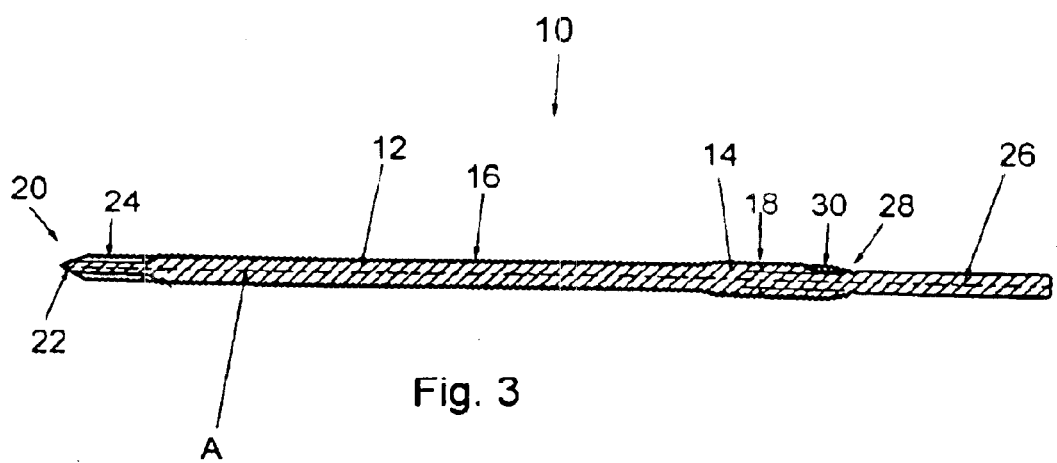
FIG. 3 is a longitudinal section view of the distraction pin according to the invention.

Turning now to FIGS. 1 through 3, an internal fixation device comprises a preferably stainless steel pin 10 having a first and second longitudinal portions 12, 14. The first portion 12 has a first diameter and threads 16 of a first thread diameter, and the second portion 14 has a relatively larger second diameter and threads 18 of a relatively larger second thread diameter. Threads 16 and 18 extend in the same rotational direction, are substantially uninterrupted along the length of the pin, and preferably are continuous with each other. That is, threads 16 preferably become threads 18 at the change in diameter from first portion 12 to second portion 14. Preferably there is no length of pin 10 between the first and second portions 12, 14 absent of threads, with the exception of the below described tip 20. In a preferred embodiment suitable for fixation of Type I and Type II distal radius fractures, the first portion has a length of approximately 2.55 inches and a diameter of approximately 0.125 inch, and the second portion has length of approximately 0.6 inch and a diameter of approximately 0.015 inch, although pins having other relative dimensions may be used.

According to a preferred aspect of the invention, the threads 16, 18 on each of the first and second portions 12, 14 have the same pitch and thread depth. A currently preferred thread pitch is forty threads per inch, and a preferred thread depth is 0.016 inch. The first portion 12 includes a self-tapping tip 20 adapted to provide increased purchase in the radial shaft cortex. The tip 20 is preferably conical and defined by a surface 22 at a 30° angle relative to the longitudinal axis A of the pin (FIG. 3). In addition, the tip 12 preferably includes three cutting flutes 24. As such, the tip is a drill as well as self-tapping.

The pin 10 does not include a conventional enlarged head portion opposite the tip 20. Rather, the pin 10 is provided with a preferably non-threaded shaft portion 26 which is preferably smaller in diameter than the second portion 14. The shaft portion 26 is a means by which to rotate the pin 10 for threaded insertion into bone. In particular, the shaft portion is adapted to be received in a chuck of a drill device. As such, the shaft portion 26 may be circular, hexagonal or any other shape in cross-section, provided it may be gripped by a rotational driving tool. The shaft portion preferably has a length of approximately 0.8 inch and a diameter of 0.09–0.10 inch.

According to another preferred aspect of the invention, the shaft portion 26 is intended to be decoupled from the second portion 14. In order to facilitate decoupling of the shaft portion 26 from the second portion 14, a circumferential channel 28 is preferably provided at the intersection of the second portion and the shaft portion. The channel is preferably approximately 0.02 to 0.03 inch wide and preferably approximately 0.025 inch deep. Then, when the shaft portion 26 is desired to be separated from the pin 10, the shaft portion may be frangibly detached from the second portion, e.g., by bending. If the shaft portion 26 cannot be frangibly separated, the channel 28 provides a guide and a purchase for a cutting instrument to act on the pin 10 to separate the shaft portion 26 from the pin. It is recognized that even if a channel is not provided to the pin, the shaft portion may nevertheless be removed by cutting.

According to yet another preferred aspect of the invention, the second portion 14 is provided with a plurality of circumferentially spaced-apart longitudinal grooves 30 adjacent its intersection with the shaft portion 26. The grooves are channels, furrows, flutes, or other preferably longitudinal negative spaces defined about the circumference of the second portion. Most preferably, three grooves 30 are provided and preferably spaced apart 120° about the circumference of the second portion 14 and preferably have a depth which extends below the threads 18.

Prior to use, if necessary, the fracture is first reduced. Then, the shaft portion 26 of the pin 10, engaged in a chuck of a drill or other rotational driving device, is percutaneously introduced to the bone and rotationally drilled through the distal fragment, across the fracture, and into the radial shaft cortex. The self-tapping tip 20 facilitates initial insertion into the bone and as well as purchase of the tip in the radial shaft cortex. The threads 16 on the first portion 12, with their particular depth and pitch, provide a stable engagement with the shaft of the radial shaft bone proximal of the fracture. As the pin is inserted further, the second portion 16 enters the distal fragment and the wider threads 18 provide superior purchase on the distal fragment of bone. The pin 10 is inserted until the intersection of the second portion 16 and the shaft portion 26 lies flush with, or more preferably slightly recessed relative to, the surface of the distal fragment. The shaft of the pin is then removed from the pin, e.g., by bending or cutting. It is noted that the headless design does not cause the distal fragment to be compressed against the radial shaft from which it separated. In addition, by providing the first and second portions 12, 14 with threads of the same pitch and thread depth, the reduction of the fracture provided by the physician is not disturbed or acted against by the screw, but rather maintained. In fact, unlike other fixation pins, the pin of the invention can be used to maintain a reduced fracture in a distracted state.

Referring to FIGS. 4 and 5, after the shaft portion has been removed from the pin, the plurality of grooves 30 are accessible at the end of the second portion. The grooves 30 provide a means for engaging the pin 10 such that, should pin removal be necessary after insertion, the headless pin can be retrieved. To that end, a driver 40 including a handle 42 and a shaft 44 provided with a socket 46 is provided. The handle 42 is preferably provided with finger engagement structure, e.g., circumferential ridges 48 and corresponding grooves 50, for gripping by the hand of a physician, as well as a rounded back 52 adapted to seat in the palm of a physician's hand. The socket 46 is adapted to be positioned over the end of the second portion 14 and provide rotational interference with the second portion. For example, the socket 46 may include internal ribs 54 adapted to rotationally interfere with the second portion 14 at the grooves 30. As such, positioning the socket 46 over the end of the second portion of the pin and rotating the driver 40 in a first direction causes extraction of the pin from the bone, while rotating the driver in an opposite second direction causes the pin 10 to be further seated (or reseated) in the bone.

Figure 6:
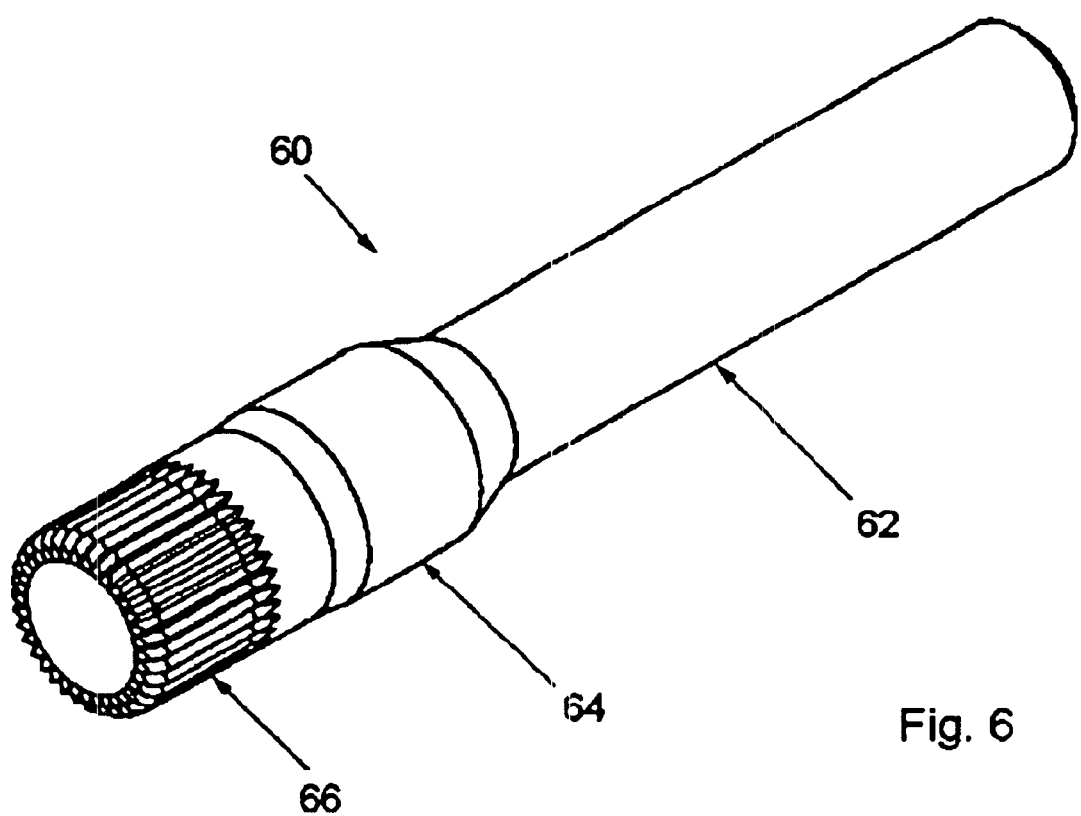
FIG. 6 is an enlarged broken perspective view a mill tool according to the invention.

Turning now to FIG. 6, it is recognized that the socket 46 has a larger diameter than the end of the second portion 14 of the pin 10. Therefore, if it is desirable to remove a recessed pin, it may be necessary to remove a small amount of bone to provide access for the socket to fit over the pin. To that end, it is preferable that a mill tool 60 be provided. The mill tool 60 includes a shaft 62 provided with a head 64 having a plurality of serrations 66 or other bone removing structure about its periphery. The serrations 66 are adapted to remove bone when the mill tool is rotated about the longitudinal axis of the shaft 62. The head 64 of the mill tool preferably has an outer diameter which is substantially equivalent to the outer diameter of the socket 46. The mill tool 60 may be provided in a handle similar to handle 42. For example, the shaft 44 of the socket 46 may be removable from the handle 42 so that the shaft 62 of the mill tool 60 may be received therein. Alternatively, a handle (not shown) which includes the mill tool 60 extending in one direction, and the socket 46 extending in another direction, e.g., an opposite direction or at an angle relative thereto, may be used.

There have been described and illustrated herein an embodiment of a fracture fixation pin. While a particular embodiment of the invention has been described, it is not intended that the invention be limited thereto, as it is intended that the invention be as broad in scope as the art will allow and that the specification be read likewise. Thus, it will be appreciated that pins of other dimensions, having one or more of the preferred aspects of the invention are in accord with the scope of the invention. In addition, while particular thread pitches and depths have been disclosed, it will be understood that the threads of the pin can have other pitches and depth. Also, while the shaft portion is preferably frangibly connected to the threaded portion, it will be recognized that the shaft portion may be otherwise coupled thereto. For example, the shaft portion can be threadably coupled to the second portion in a manner in which the shaft portion and second portion are coupled when the shaft portion is rotated in the first rotational direction and threadably uncoupled when the shaft portion is rotated in the second rotational direction. Alternatively, the shaft portion may be interference fit in a socket at the end of the second portion. For example, the shaft portion may have a hex wrench end and the second portion may have a hex socket end into which the hex wrench end is received. It will therefore be appreciated by those skilled in the art that yet other modifications could be made to the provided invention without deviating from its spirit and scope as claimed.

What is claimed is:

1. A fracture fixation pin, comprising:
   a) a solid first portion having a first diameter and first threads of a first thread diameter, said first portion having a tip at one end and a second end;
   b) a solid second portion coupled to said second end of said first portion, said second portion having a second diameter larger than said first diameter, and second threads of a second thread diameter larger than said first thread diameter, said second threads extending in a same direction as said first threads; and
   c) a solid non-threaded shaft portion coupled to said second portion, said shall portion having a cross-sectional dimension which does not exceed a dimension of said second diameter,
      wherein said second portion is provided with a plurality of longitudinal grooves extending crosswise through at least one of said second threads, said grooves being located adjacent said shaft portion and spaced-apart about an outer circumference of said second portion.

2. A fracture fixation pin according to claim 1, wherein: said first and second threads are continuous.

3. A fracture fixation pin according to claim 1, wherein: said tip includes a plurality of cutting flutes.

4. A fracture fixation pin according to claim 1, wherein: said tip is substantially conical and includes a surface angled at 30° relative to a longitudinal axis.

5. A fracture fixation pin according to claim 1, wherein: said first portion has a first length of approximately 2.55 inches and a first diameter of approximately 0.125 inch, and said second portion has a second length of approximately 0.6 inch and a second diameter of approximately 0.156 inch.

6. A fracture fixation pin according to claim 1, wherein: said shaft portion is substantially cylindrical.

7. A fracture fixation pin according to claim 1, wherein: said shaft is frangibly coupled to second portion.

8. A fracture fixation pin according to claim 1, wherein: a channel is provided about said pin between said second portion and said shaft portion.

9. A fracture fixation pin according to claim 1, wherein: said shaft has cross-sectional dimension smaller than said second diameter of said second portion.

10. A fracture fixation pin according to claim 1, wherein: said pin is not provided with a head portion.

11. A fracture fixation pin according to claim 1, wherein: all threads on said first portion have said first thread diameter.

12. A fracture fixation pin according to claim 1, wherein: said pin is made of metal.

13. A fracture fixation pin according to claim 1, wherein: said plurality of grooves includes exactly three grooves spaced apart 120° about said circumference of said second portion.

14. A fracture fixation pin according to claim 1, wherein: each of said grooves has a depth which extends below said second threads.

15. A fracture fixation pin system, comprising:
a) a pin including
   i) a first portion having a first diameter and first threads of a first thread diameter, said first portion having a tip at one end and a second end,
   ii) a second portion coupled to said second end of said first portion, said second portion having a second diameter larger than said first diameter, and second threads along substantially an entirety thereof, said second threads of a second thread diameter larger than said first thread diameter, said first and second threads being continuous with each other and having a common pitch and thread depth, and
   iii) a non-threaded shaft portion coupled to said second portion, said shaft portion having a cross-sectional dimension which does not exceed a dimension of said second diameter,
   said second portion adjacent said shaft portion defining a plurality of longitudinal spaced apart negative spaces about an outer circumference thereof; and
b) a driver member including a socket having structure adapted to interfere with said negative spaces.

16. A fracture fixation pin system according to claim 15, further comprising:

c) a mill tool having structure adapted to remove bone and define an opening in the bone into which said socket of said driver member can be inserted.

17. A fracture fixation pin, comprising:
a) a first portion having a first diameter and first threads of a first thread diameter, said first portion having a tip at one end and a second end; and
b) a second portion having a first end coupled to said second end of said first portion and a second free end, said second portion having a second diameter larger than said first diameter, and second threads of a second thread diameter larger than said first thread diameter, said first and second threads being continuous with each other and having a common pitch and thread depth, wherein said second free end is provided with a plurality longitudinal grooves spaced-apart about an outermost circumference of said second portion and extending crosswise through at least one of said second threads.

18. A fracture fixation pin according to claim 17, wherein:
said plurality of grooves includes three grooves spaced apart 120° about said circumference of the second portion.

19. A fracture fixation pin according to claim 17, wherein:
each of said grooves has a depth which extends below said second threads.

20. A fracture fixation pin system, comprising:
a) a one-piece pin including
  i) a non-hollow first portion having a first diameter and first threads of a first thread diameter, said first portion having a tip at one end and a second end, and
  ii) a non-hollow second portion having a first end coupled to said second end of said first portion and a second free end, said second portion having a second diameter larger than said first diameter, and second threads of a second thread diameter larger than said first thread diameter, said first and second threads being continuous with each other and having a common pitch and thread depth, wherein said second free end is provided with a plurality of longitudinal grooves spaced-apart about an outer circumference of said second portion; and
b) a driver member including a socket having structure adapted to interfere with said grooves on said second portion of said pin.

21. A fracture fixation pin system according to claim 20, further comprising:
c) a mill tool having structure adapted to remove bone and define an opening in the bone into which said socket of said driver member can be inserted.

* * * * *